(12) United States Patent
Fattori et al.

(10) Patent No.: US 6,347,425 B1
(45) Date of Patent: Feb. 19, 2002

(54) POWERED TOOTHBRUSH HAVING THREE DIMENSIONAL ROTATIONAL HEAD MOTION

(75) Inventors: Joseph Fattori, Mendham; Kenneth Waguespack, North Brunswick, both of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/605,188

(22) Filed: Jun. 28, 2000

(51) Int. Cl.[7] ............................. A46B 7/06; A46B 7/08
(52) U.S. Cl. ............................. 15/22.1; 15/28
(58) Field of Search ........................ 15/21.1, 22.1, 15/22.4, 28, 29

(56) References Cited

U.S. PATENT DOCUMENTS

| | | | |
|---|---|---|---|
| 1,255,028 A | | 1/1918 | Leonard et al. |
| D223,945 S | * | 6/1972 | Bousquet |
| 4,156,620 A | | 5/1979 | Clemens |
| 4,479,516 A | | 10/1984 | Hunter |
| 5,173,983 A | * | 12/1992 | Le |
| 5,416,942 A | | 5/1995 | Baldacci et al. |
| 5,504,961 A | | 4/1996 | Yang |
| 5,625,916 A | * | 5/1997 | McDougall |
| 5,862,558 A | | 1/1999 | Hilfinger et al. |
| 5,867,856 A | | 2/1999 | Herzog |
| 5,974,613 A | * | 11/1999 | Herzog |
| 6,092,252 A | * | 7/2000 | Fisher et al. |

* cited by examiner

*Primary Examiner*—Terrence R. Till
(74) *Attorney, Agent, or Firm*—Henry S. Goldfine

(57) ABSTRACT

An electrically driven toothbrush having a rotatable drive shaft with an end, off-set from the central longitudinal axis of the drive shaft and lodged in a boring in a bristle carrier, which bristle carrier is orbitally secured within a socket in the toothbrush head. When the drive shaft rotates, the end describes a circle and drivingly engages the bristle carrier to actuate the bristle carrier in a three dimensional reciprocating side-to-side and rocking up-and-down motion.

12 Claims, 5 Drawing Sheets

POWERED TOOTHBRUSH HAVING THREE DIMENSIONAL ROTATIONAL HEAD MOTION

FIELD OF THE INVENTION

This invention relates to electrically powered toothbrushes and more particularly to such toothbrushes having a head which provides a three dimensional reciprocating side-to-side and rocking up-and-down motion.

BACKGROUND OF THE INVENTION

Conventional electric toothbrushes having generally cylindrical brush heads operate by means of a direct current motor, wherein the rotational motion of the motor is translated into a two dimensional, typically, rotationally clockwise and counterclockwise reciprocating movement. As disclosed in U.S. Pat. No. 4,156,620, the unidirectional, axial motion of the drive shaft of a direct current motor, can initially be converted into a circular motion by means of a pinion and crown gear assembly. The circular motion can then be translated into a reciprocating motion to correspondingly drive the brush head by means of attaching to the crown gear a crank arm and clevis assembly. This is a complex mechanism, which is relatively costly to produce and has a high potential for mechanical failure.

U.S. Pat. No. 5,625,916 discloses a simplified electric toothbrush drive mechanism, wherein the end of the drive shaft is in the form of an elbow, i.e. bent away from and partially back toward its own longitudinal axis, and disposed within a slot in a cylindrical brush head; which slot is parallel to the longitudinal axis of the cylindrical brush head. As the drive shaft rotates unidirectionally, the elbow will describe a corresponding unidirectional circle about the longitudinal axis of the drive shaft, traveling up and down relative to the longitudinal axis of the cylindrical brush head, such that it drivingly engages the side edges of the slot to cause the cylindrical brush head to reciprocate side-to-side in two dimensions. Such a two dimensional reciprocating action limits the duration of contact between the bristle tufts and the three dimensional dentiture of the user, limiting the cleaning efficacy of the toothbrush.

U.S. Pat. No. 5,862,558 discloses a powered toothbrush head having a three dimensional motion, wherein the bristle ends rotate in a cone shape for enhanced cleaning. To achieve this three dimensional cone shaped rotation, U.S. Pat. No. 5,862,558 utilizes a complex mechanism involving two bearing pins (one transverse to the longitudinal axis of the toothbrush and the other angled thereto), a contrate gear and pinion assembly, and a tapered disk. Such a complex mechanism has the same failings as in the case of U.S. Pat. No. 4,156,620, discussed above, i.e. costly to produce and with a high potential for mechanical failure.

There is an ongoing need in the art for an electric toothbrush having a simplified mechanism and that provides a three dimensional head motion to conform the bristles more closely to the teeth for enhanced cleaning thereof.

BRIEF SUMMARY OF THE INVENTION

The present invention provides a mechanically simplified electrically powered toothbrush having an elongated body with a head at one end and a handle at the other; the head containing a socket having curved sides; the socket containing a bristle carrier orbitally disposed therein; the bristle carrier having an upper surface with a plurality of bristle tufts extending therefrom and sides with a curvature corresponding to the curved sides of the socket; the bristle carrier being provided with a boring in the sides thereof; the handle being arranged to contain a rotational driving means with a drive shaft extending therefrom and ending in a end which is displaced from the central longitudinal axis of the drive shaft and is drivingly engaged in the boring; whereby, upon rotation of the drive shaft the bristle carrier is driven by the end in a three dimensional, reciprocating side-to-side and rocking up-and-down motion within the socket. This three dimensional movement of the toothbrush head increases contact between the bristles and the three dimensional surfaces of the teeth for enhanced cleaning thereof.

DETAILED DESCRIPTION OF THE PREFERRED EMBODIMENTS

Figure 1:
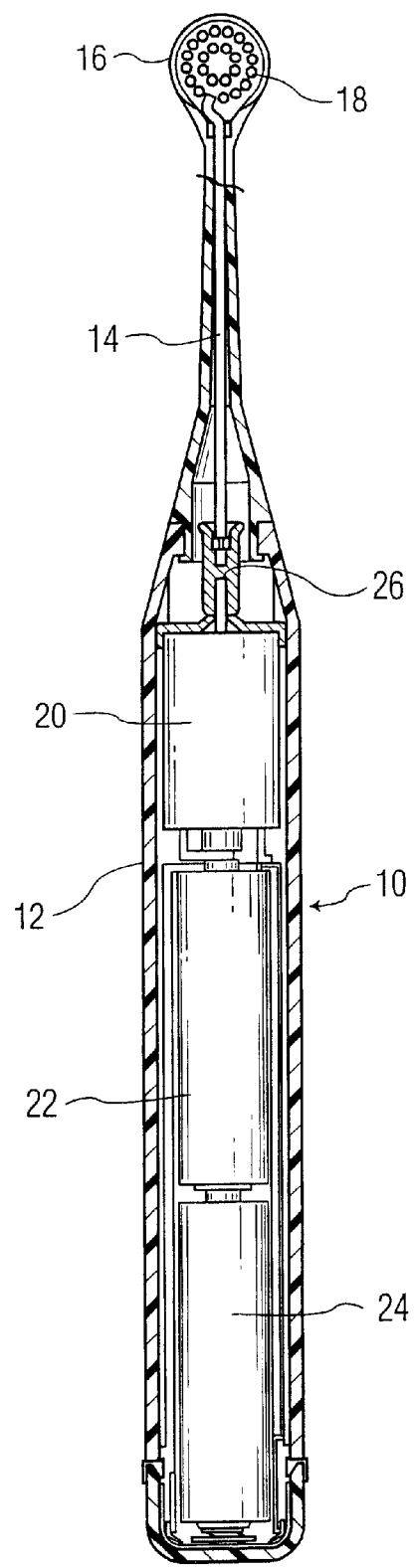
FIG. 1 is a front sectional view of an embodiment of the toothbrush of the present invention.

Referring to the drawings, wherein like reference numerals refer to the same or similar elements among the several figures, and in particular to FIG. 1; wherein there is shown an electric toothbrush, 10, in accordance with the present invention. The toothbrush, 10, comprises a handle 12 at a first end of the toothbrush, a head 16 at a second end of the toothbrush, a rotatable cylindrical drive shaft 14 extending from the handle 12 to the head 16, and a bristle carrier 18 disposed within the head 16. The bristle carrier 18 has a flat or partially flat upper surface from which extend a plurality of bristle tufts 30, a lower surface 32 and sides 48 with a spherical curvature, wherein the cross-section at the midpoint or apex of said spherical curvature is circular and lies in a plane passing through the center 42 of the bristle carrier 18. The handle 12 provides compartments for holding an electric motor 20 and two batteries 22 and 24, providing a preferred means to power the toothbrush, and may also contain an electrical switch (not shown) to activate and deactivate the motor. A conventional shaft coupling 26 is arranged to connect the drive shaft 14 to the motor 20, and if desired, allows a means to demount the head 16 from the handle 12, such that a replacement head can be utilized when the bristles 30 become worn.

Figure 2:
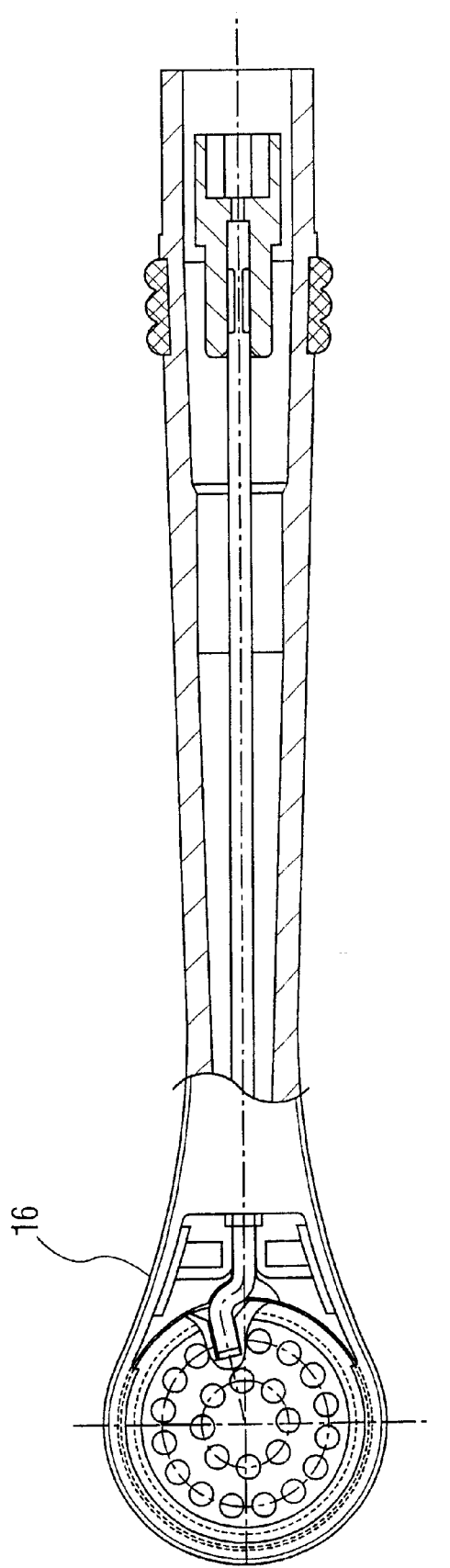
FIG. 2 is a front view of the head thereof, showing sectional images of the bristle carrier and its connection to the drive shaft.
Figure 3:
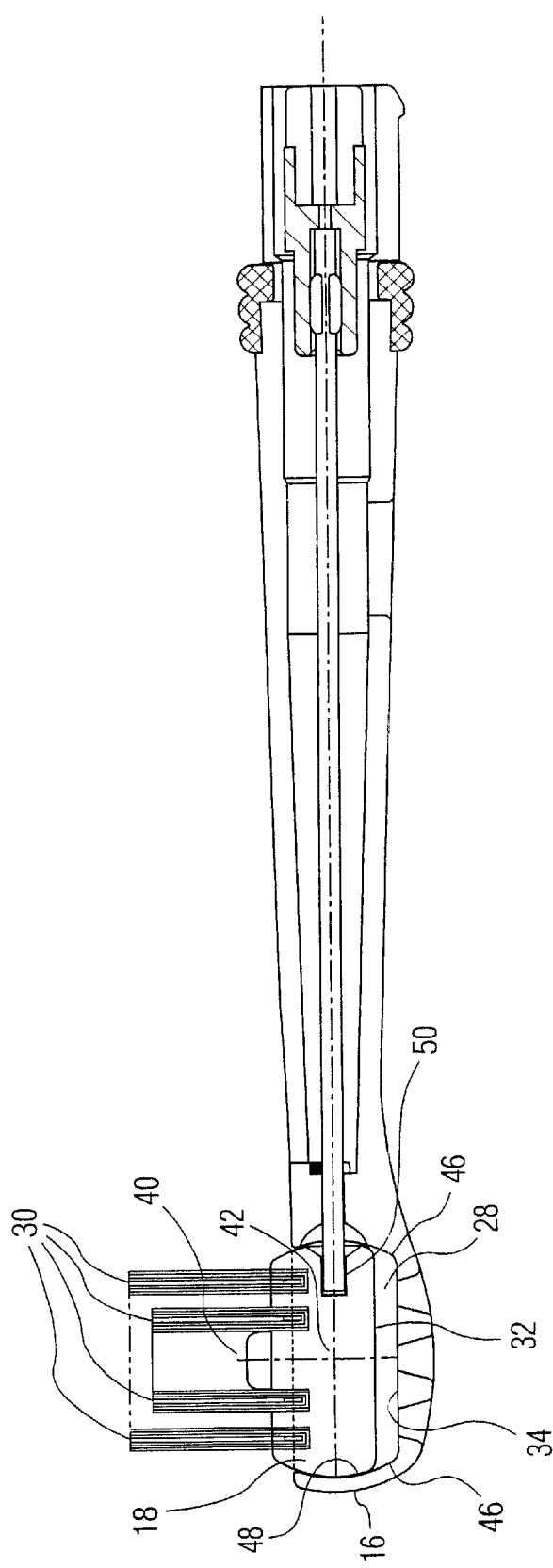
FIG. 3 is a left side sectional view of the head thereof, wherein the bent end of the drive shaft is aligned within the horizontal plane containing the longitudinal axis of the drive shaft, at a position of 9 o'clock in relation to the horizontal plane containing the central longitudinal axis of the drive shaft; the right side sectional view is a mirror image of the view of FIG. 3.

The head 16, as viewed in FIGS. 2 and 3, contains a cavity or socket 28 having an open top, a generally flat or convex bottom 34, and smooth convexly curved spherical sides 46 to provide a housing within which the bristle carrier 18 is disposed and can three dimensionally, i.e. orbitally, rotate.

To facilitate such orbital movement of the bristle carrier 18 within the socket 28, the side 48 of the bristle carrier 18 has a smooth convex spherical curvature closely aligned to that of the spherically curved sides 46 of the socket 28. Further, the bristle carrier 18 is positioned within the socket 28 such that there is clearance between the bottom surface of the bristle carrier 32 and the lower surface of the socket 34. This clearance allows one side of the bristle carrier 18 to orbitally rotate downward into the socket, while the second, opposite side orbially rotates upward out of the socket 28, see FIGS. 4 and 5.

Figure 4:
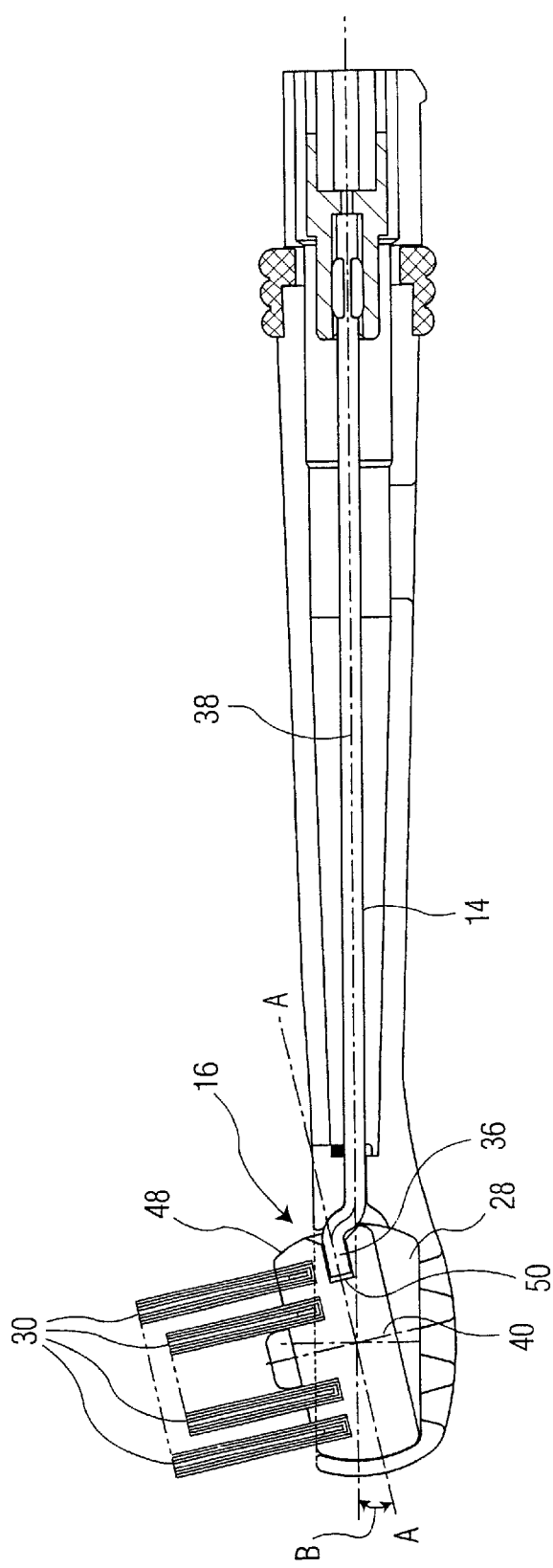
FIG. 4 is a left side sectional view of the head thereof, wherein the bent end of the drive shaft is at a position of 12 o'clock in relation to the horizontal plane containing the central longitudinal axis of the drive shaft.
Figure 5:
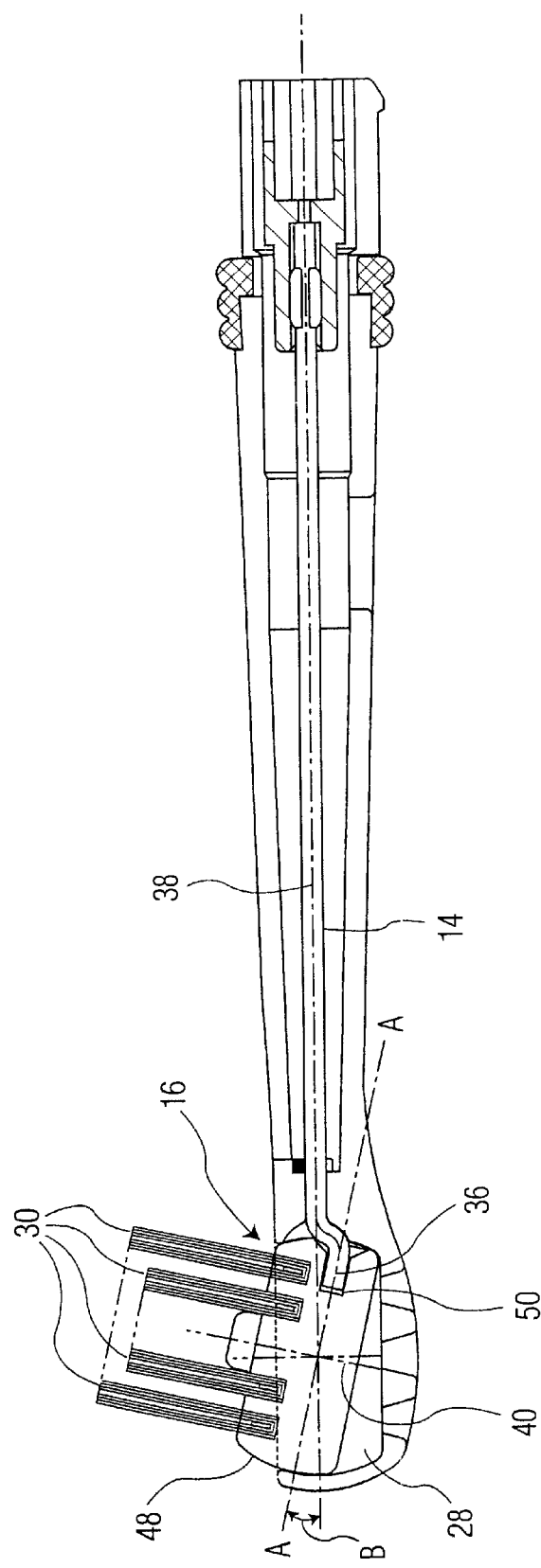
FIG. 5 is a left side sectional view of the head thereof, wherein the bent end of the drive shaft is at a position of 6 o'clock in relation to the horizontal plane containing the central longitudinal axis of the drive shaft.

Referring now to FIGS. 4 and 5, the position of the bristle carrier 18 within the head 16 is maintained and controlled by the bent end 36 of the drive shaft 14 which is rotatably lodged in a boring 50, which boring is preferably cylindrical and extends radially inward from the outer circumference of the bristle carrier 18. The cross-section of the boring 50 is preferably generally the same as the cross-section of the bent end 36, to leave minimum play therebetween. The bent end 36 is displaced or off-set from a central longitudinal axis 38 of the drive shaft 14 and bent back toward the central longitudinal axis 38, such that the bent end 36 points along an axis A-A toward the central point 42 of the bristle carrier 18. The bristle carrier has a central axis 40 which passes through the central point 42 of the bristle carrier 18 and which is perpendicular to the plane in which the mid-point circular cross-section lies.

An angle β is formed between the axis A—A and the central longitudinal axis 38. Angle β is shown in FIGS. 4 and 5 at a preferable 12.5 degrees, wherein the bent end 36 is bent toward the central longitudinal axis 38 at an angle of 77.5 degrees, the complementary angle to angle β. As the bent end 36 is rotated by the drive shaft 14, it describes a circle about the central longitudinal axis 38, thereby driving the bristle carrier 18 in reciprocating side-to-side and rocking up-and-down arcs commensurate to angle β, such that, at the preferred angle β of 12.5 degrees, the arc will circumscribe 25 degrees side-to-side and up-and-down. The off-set of the bent end 36 can be varied such that angle β can be from about 5 to about 20 degrees, i.e. the bent end 36 can correspondingly be bent toward the central longitudinal at an angle of from 85 to 70 degrees; so that the bristle carrier 38 will resultingly be driven in a lesser or greater rocking up-and-down and reciprocating side-to-side three dimensional motion about the central point 42. The relative position of the bent end 36 in relationship to the resulting rocking up-and-down motion of the bristle carrier 18 can be seen in FIGS. 3, 4 and 5, as the bent end 36 is rotated.

Within the brush head 16 shown in FIGS. 3, 4 and 5, the bristle carrier 18 has a plurality of bristle tufts extending from the upper surface thereof, wherein the outer bristles about the periphery of the bristle carrier 18 are preferably longer than the inner bristles closer to the center of the brush head 16; providing a recess within the surface defined by the bristle ends to hold the quantity of toothpaste applied to the toothbrush and to conform to the curved surfaces of each tooth. Notwithstanding this length relationship of the inner and outer bristles, the particular bristles pattern shown is arbitrary and merely for illustrative purposes.

The motor, 20, as seen in FIG. 1 is preferably run at about 2,200 rpm, in order to provide a reciprocating motion of the bristle carrier 18 of about 4,400 complete side-to-side and up-and-down oscillations per minute about the central point 42. Where desired the motor can be run at other speeds of from about 800 rpm up to and over about 4,500 rpm, or the motor can be arranged to run at two or more speeds selectable by the user.

To provide a smooth rotation of the bristle carrier 18, within the socket 28, the bristle carrier 18 and the brush head 16 including the socket 28 are preferrably manufactured of a plastic with a low coefficient of friction and good wear characteristics. A preferred variety of such plastic is acrylonitrile-butadiene-styrene, ABS, copolymers, available under the grade designation PA757 from the Chi Mei Corporation, Jen Te, Taiwan, ROC. A particularly preferred variety of such plastic is polyacetals, such as polyoxymethylene, POM, available under the tradename of Delrin, grade 500P, from DuPont Engineering Polymers, Wilmington, Del. 19898.

What is claimed is:

1. An electrically powered toothbrush (10) comprising:
   an elongated body having a head (16) at one end and a handle (12) at the other end; the head (16) containing a socket (28) having curved sides (46) and a bristle carrier (18) disposed therein;
   the bristle carrier (18) having an upper surface with a plurality of bristle tufts (30) extending therefrom and sides (48) curved to correspond to the curved sides (46) of said socket (28);
   the bristle carrier (18) having a boring (50) in a side (48);
   said handle (12) containing a drive means with a drive shaft (14) extending therefrom to an end (36) which is displaced from the central longitudinal axis (38) of the drive shaft (14) and which is drivingly engaged in said boring (50); whereby, upon rotation of said drive shaft (14) by said drive means, the end (36) actuates the bristle carrier (18) in at least two motions to effect a three dimensional movement of the bristle carrier (18) within the socket (28).

2. An electrically powered toothbrush (10) according to claim 1, wherein said socket (28) has spherically curved sides (46).

3. An electrically powered toothbrush (10) according to claim 2, wherein the end (36) is angled towards the central longitudinal axis (38) by an angle of about 77.5 degrees.

4. An electrically powered toothbrush (10) according to claim 1, wherein said drive means is a rotational drive means.

5. An electrically powered toothbrush (10) according to claim 3, wherein said rotational drive means is an electric motor (20).

6. An electrically powered toothbrush (10) according to claim 1, wherein said at least two motions are a reciprocating motion and a rocking motion.

7. An electrically powered toothbrush (10) according to claim 6, wherein said reciprocating motion is a side-to-side motion.

8. An electrically powered toothbrush (10) according to claim 6, wherein said rocking motion is an up-and-down motion.

9. An electrically powered toothbrush (10) according to claim 1, wherein
   the bristle carrier (18) has a central axis (40);
   the end (36) points towards the intersection of the central longitudinal axis (38) and the central axis (40) and the end (36) is angled towards the central longitudinal axis (38) by an angle of about 70 to about 85 degrees.

10. An electrically powered toothbrush (10) according to claim 1, wherein the drive shaft (14) is rotated at about 800 to about 4,500 rpm.

11. An electrically powered toothbrush (10) according to claim 1, wherein the drive shaft (14) is rotated at about 2,200 rpm.

12. An electrically powered toothbrush (10) according to claim 1, wherein the head (16) and the bristle carrier (18) is formed from a acrylonitrile-butadiene-styrene or polyoxymethylene copolymer.

* * * * *